United States Patent [19]
Umeno et al.

[11] Patent Number: 5,569,200
[45] Date of Patent: Oct. 29, 1996

[54] VASCULAR CATHETER

[75] Inventors: Akihiko Umeno; Takahiro Kugo, both of Fujinomiya, Japan

[73] Assignee: Terumo Kabushiki Kaisha, Tokyo, Japan

[21] Appl. No.: 492,396

[22] Filed: Jun. 19, 1995

[30] Foreign Application Priority Data

Jun. 20, 1994 [JP] Japan .................................. 6-137273

[51] Int. Cl.$^6$ ........................................................ A61M 5/00
[52] U.S. Cl. ........................... 604/96; 604/282; 606/194
[58] Field of Search .............................. 604/96, 280, 281, 604/282, 264, 101, 102, 103; 606/190–194

[56] References Cited

U.S. PATENT DOCUMENTS

| | | | |
|---|---|---|---|
| 5,364,357 | 11/1994 | AAse | 604/96 |
| 5,382,234 | 1/1995 | Cornelius et al. | 604/96 |
| 5,451,209 | 9/1995 | Ainsworth et al. | 604/282 |
| 5,456,665 | 10/1995 | Postell et al. | 604/96 |
| 5,458,605 | 10/1995 | Klemm | 604/282 X |

FOREIGN PATENT DOCUMENTS

| | | |
|---|---|---|
| 0437795 | 12/1990 | European Pat. Off. . |
| 0608853 | 1/1994 | European Pat. Off. . |
| 0631791 | 6/1994 | European Pat. Off. . |
| 4104092 | 2/1990 | Germany . |
| 61-228878 | 1/1986 | Japan . |
| 3-081390 | 12/1991 | Japan . |

*Primary Examiner*—John D. Yasko
*Attorney, Agent, or Firm*—Burns, Doane, Swecker & Mathis, LLP

[57] ABSTRACT

A vascular catheter includes a catheter body which is made up of an inner tube formed of a metal or a alloy and an outer tube formed of a synthetic resin covering the outside surface of the inner tube. The inner tube has one or more spiral slits in the distal end portion. A vascular dilatation instrument includes an inner tube, an outer tube disposed coaxially around the inner tube, an inflatable member having one end attached to the inner tube and another end attached to the outer tube. At least one of the inner tube and the outer tube includes a main body section based on a tube formed of a metal or alloy and a distal section made of a synthetic resin. The tube made of the metal or the alloy has one or more spiral slits in the distal end portion. The metal is selected from the grope consisting of steel, tungsten and copper. The alloy is selected from the grope of steel alloy, tungsten alloy and copper alloy.

6 Claims, 6 Drawing Sheets

VASCULAR CATHETER

FIELD OF THE INVENTION

The present invention relates to a vascular catheter used for intravascular surgical operation, highly localized injection of medicine such as anticancer drugs, and angiography.

BACKGROUND OF THE INVENTION

Recently, intravascular surgical operation using vascular catheters has practiced for treating aneurysm and anteriovenous malformation (AVM) instead of ordinary surgical operation. A vascular catheter for this purpose must be inserted to the intended part of a blood vessel being passed in complicatedly bent or branched blood vessels.

For such a vascular catheter, high manipulability to insert it easily and quickly up to a target lesion passing in complicatedly bent or branched small blood vessel is required.

To have high manipulability, a vascular catheter must have the following four properties.

The first property is that the catheter can convey the pushing force in the direction of the axis added to the proximal end portion by the operator up to the distal end or has so called pushability.

The second property is that the catheter can convey the turning force around the axis added to the proximal end portion up to the distal end or has so called turnability.

The third property is that the catheter can be advanced in blood vessels along the guide wire inserted beforehand easily and without causing damage to the wall of the blood vessels or has so called pliability.

The fourth property is that the catheter does not kink at bents (curves and crooks) in blood vessels after the guide wire is removed or has reluctance to kinking.

J.P.B.3-81,390 discloses a catheter having a spiral reinforcement made of synthetic fibers embedded on the catheter. The catheter has reluctance to kinking, but the catheter has not good pushability and good turnability.

J.P.A.61-228,878 discloses a catheter having a spiral reinforcement made of metal embedded on a distal portion of the catheter. The spiral reinforcement has a repulsive power. The repulsive power causes a distortion of the distal portion of the catheter. Therefore, the catheter has not good turnability. In this catheter, it is difficult to be balanced between flexibility and reluctantly to kinking.

SUMMARY OF THE INVENTION

The first object of this invention is to provide a vascular catheter which has improved turnability, flexibility and reluctance to kink.

The second object of this invention is to provide a vascular dilatation instrument which has improved turnability, flexibility and reluctance to kink.

The vascular catheter of the present invention comprises a catheter body which is made up of an inner tube formed of a metal selected from the grope consisting of steel, tungsten and copper or a alloy selected from the grope of steel alloy, tungsten ahoy and copper alloy and an outer tube formed of a synthetic resin covering the outside surface of the inner tube and has a lumen, said catheter body has a main portion and a tip portion, the main portion of the catheter body is made up of the inner and outer tubes, the tip of the catheter body is made up of the portion of said outer tube extending from the, distal end of the inner tube, and the inner tube has one or more spiral slits in the distal end portion.

The vascular dilatation instrument of the present invention comprises an inner tube defining a first lumen extending between an open distal end and a proximal portion, an outer tube disposed coaxially around said inner tube, having a distal end retracted a predetermined distance from the distal end of said inner tube and a proximal portion, and defining a second lumen with the outside surface of said inner tube, an inflatable member having one end attached to said inner tube and another end attached to said outer tube, and defining an interior space in fluid communication with said second lumen in the vicinity of the other end, a first opening disposed in the proximal portion of said inner tube in communication with said first lumen, and a second opening disposed in the proximal portion of said outer tube in fluid communication with said second lumen, wherein at least one of said inner tube and said outer tube includes a main body section based on a tube formed of a metal selected from the grope consisting of steel, tungsten and copper or a ahoy selected from the grope of steel ahoy, tungsten alloy and copper alloy tube and a distal section made of a synthetic resin, the tube made of said metal or said alloy has one or more spiral slits in the distal end portion.

DETAILED DESCRIPTION OF THE PREFERRED EMBODIMENTS

The vascular catheter of the present invention is illustrated below in detail with the preferred embodiments shown in the attached drawings.

Figure 1:
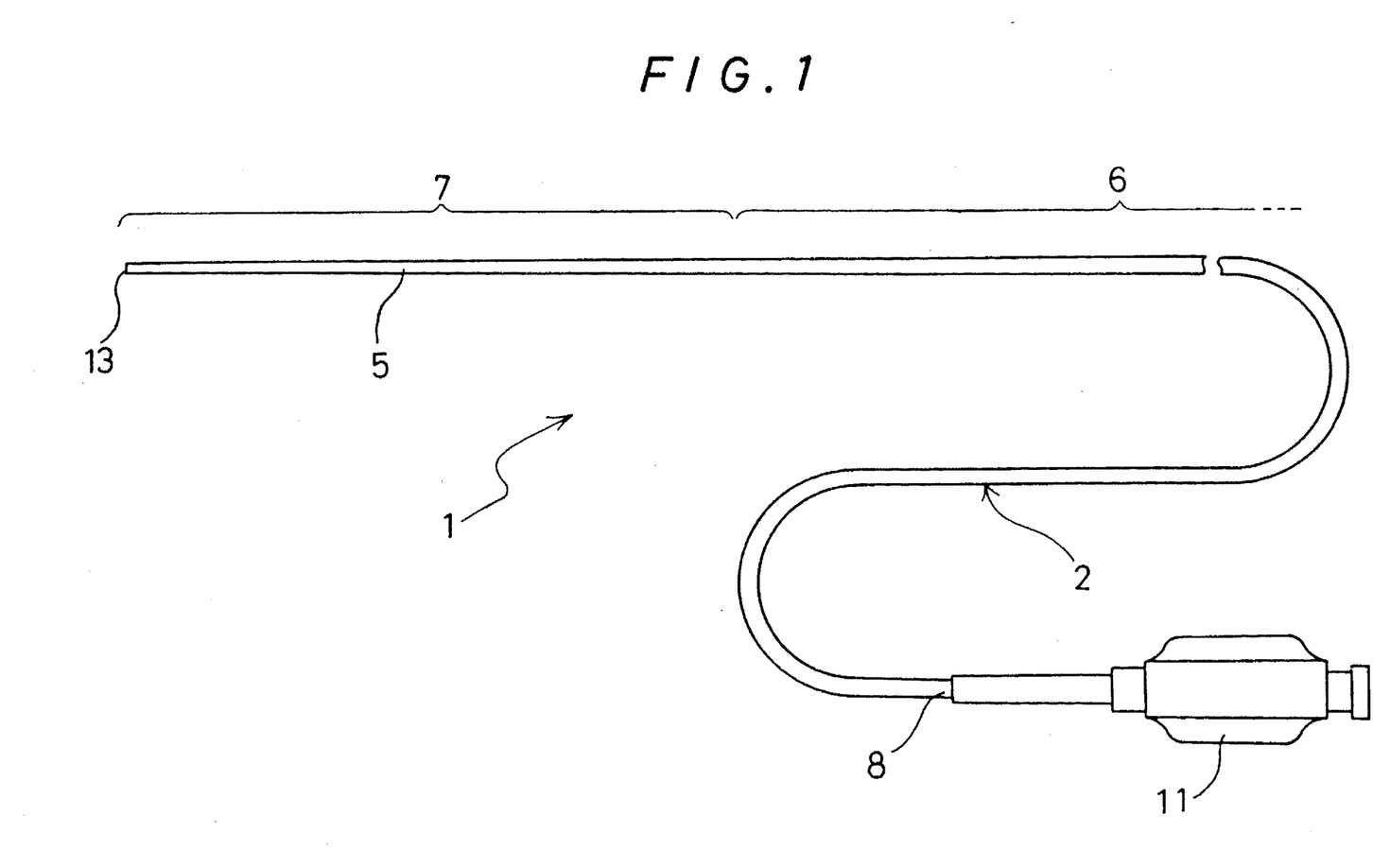
FIG. 1 is a plan view of an embodiment of the vascular catheter of an embodiment of the present invention.
Figure 2:
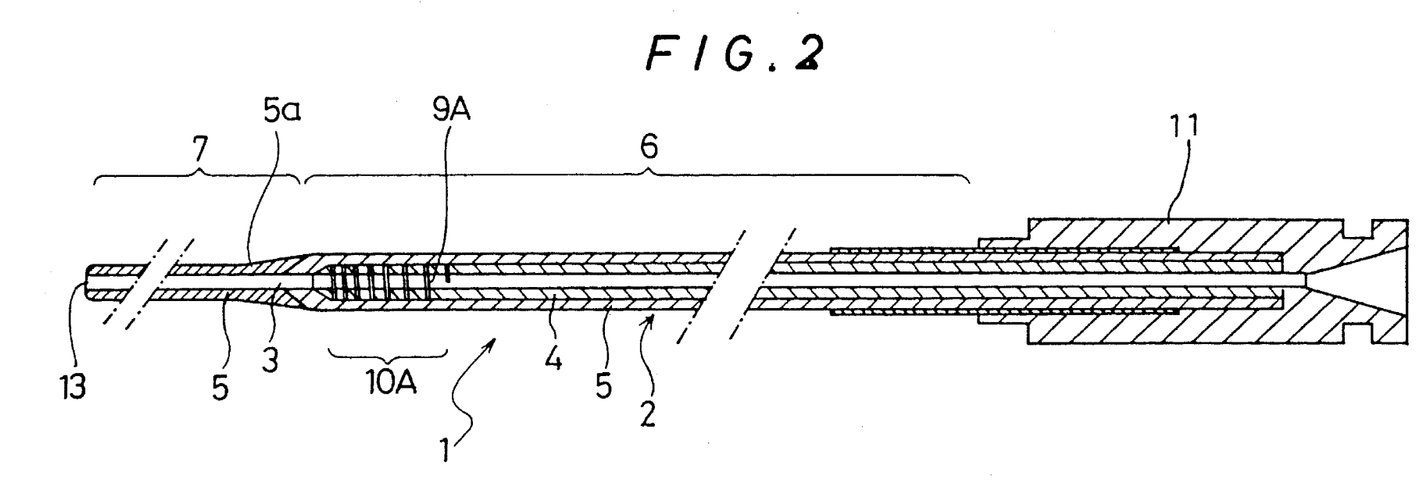
FIG. 2 is a longitudinal sectional view of the vascular catheter shown in FIG. 1.
Figure 3:
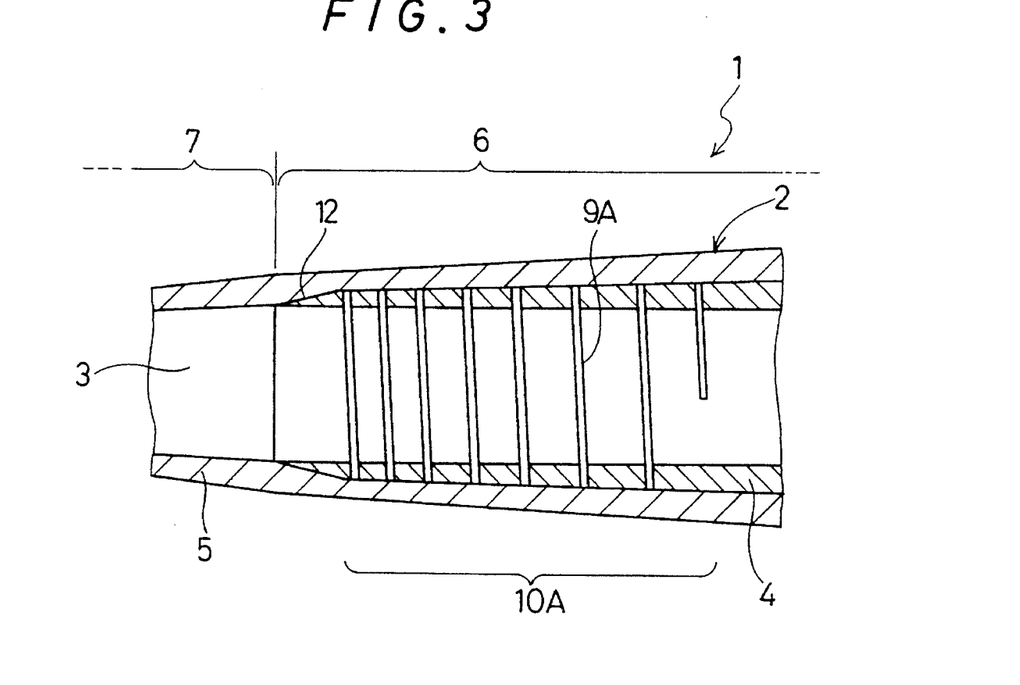
FIG. 3 is an enlarged longitudinal sectional view of the distal end portion of the vascular catheter shown in FIG. 1.

FIG. 1 is a plan view of an embodiment of the vascular catheter of the present invention. FIG. 2 is a partial longitudinal sectional view of the vascular catheter shown in FIG. 1 which shows the proximal and distal end portions of the catheter. FIG. 3 is an enlarged longitudinal sectional view of the distal end portion of the vascular catheter shown in FIG. 1 with the radial dimension enlarged at a larger ratio than the axial dimension in order to show the structure clearly.

The vascular catheter 1 of the present invention comprises a catheter body 2 and a hub 11 attached to the proximal end 8 of the catheter body 2 as shown in FIGS. 1 and 2.

The catheter body 2 has a lumen 3 formed from the proximal end 8 to the distal end 13. When the vascular catheter 1 is inserted into the blood vessel of a patient, a guide wire is passed through the lumen 3. The lumen 3 serves as the conduit for medicine or other liquid after the catheter is inserted. The hub 11 serves as the entrance for a guide wire and the inlet for medicine or other liquid into the lumen 3. The hub 11 is also used as the grip for manipulating the vascular catheter 1.

The catheter body 2 consists of a base or main portion 6 and a tip portion 7. The main portion 6 has a double-tube structure formed by an inner tube 4 and an outer tube 5 closely fitted over and bonded to an outside surface of the inner tube 4. The tip portion 7 of the catheter is formed by the outer tube 5 alone, that is, by a distal end portion of the outer tube 5 which extends beyond a distal or tip end of the inner tube 4.

In the embodiment shown in FIG. 3, a slit portion 10A having a spiral slit 9A is formed of the distal end portion of the inner tube 4 over an appropriate length from the distal end toward the proximal end. Since the width of the slit 9A changes (widens or narrows) when the slit portion 10a is subjected to an external force thereby decreasing the stress in the wall, the entire slit portion becomes more flexible. Therefore, the bending force applied to the distal end portion of the catheter when the distal end is passed through bends in blood vessel is dispersed into a larger portion (the slit portion) and kink at the boundary portion between the comparatively rigid main portion 6 of the double-tube structure and the comparatively flexible tip portion 7 of the single-tube structure caused by the concentration of stress can be prevented.

In the embodiment shown in FIG. 2 and FIG. 3, the pitch of the slit 9A becomes gradually smaller toward the distal end 13. By thus forming the slit 9A, the flexibility of the catheter body 2 increases gradually toward the distal end 13, and kink at the aforementioned boundary can be prevented with higher reliability. The pitch may be uniform throughout the length of the slit 9A.

The width and the pitch of the spiral slit 9A of the catheter 1 of this embodiment is appropriately determined by taking into account the outer diameter of the inner or outer tubes. The width is preferably within the range of about 1/10 to 1/1 times of the outer diameter of the inner tube 4. For a preferred embodiment, the width of the slit 9A is preferably within the range of about 0.01 to 1.50 mm and more preferably about 0.05 to 1.00

The pitch is preferably within the range of about 0.3 to 3 mm for the distal end portion of the slit portion 10A and about 5 to 10 mm for the proximal end portion. The pitch of the middle portion may be an intermediate value between the pitches of both end portions or may become gradually smaller from the pitch of the proximal end portion to that of the distal end portion.

The length of the slit portion 10A ( the length from the distal end of the inner tube to the proximal end of the slit) is preferably the range of about 100 to 1,000 mm and more preferably about 150 to 500 mm.

The slit 9A may be formed from the distal end of the inner tube 4 or from a position at an appropriate distance from the distal end of the inner tube 4 as the slit 9A of the embodiment shown in FIG. 3. The distance between the distal end of the inner tube 4 and that of the slit 9A is preferably up to 10 mm and more preferably up to 5 mm. The catheter of this embodiment has one slit 9A, but two or more slits may be formed the distal end portion of the inner tube.

In this embodiment, the inner diameter of the catheter body 2 (diameter of the lumen 3) is substantially uniform throughout the length of the main portion 6. The outer diameter of the catheter body 2, on the other hand, is substantially uniform throughout the almost entire length of the main portion 6 except the distal end portion (an appropriate length of portion from the distal end).

The distal end portion of the main portion 6 and the corresponding distal end portion of the inner tube 4 become gradually thinner in wall thickness to their distal ends so that this portion of the catheter body 2 gradually tapers to the distal end of the main portion 6 as shown in FIG. 3.

Further, in this embodiment, the distal end of the inner tube 4 is formed in a comparatively steep taper 12, and hence the outer diameter and wall thickness of this tappered end become smaller abruptly. As the result, the inner diameter of this portion of the outer tube 5 becomes smaller at the large diminishing rate, while the outer diameter decreases gradually as described above.

The tip portion 7 of the catheter 1 is formed by the distal end portion 5a of the outer tube 5 which extends beyond the distal end of the inner tube 4. The outer diameter of the tip portion 7 becomes gradually smaller toward the distal as shown in FIG. 1, and the wall thickness of the tip portion 7 also decreases gently toward the distal end, as shown in FIG. 3.

By thus gently tapering the outside surface of the distal end portion of the main portion 6 and tip portion 7 toward the distal end along the axis and moreover decreasing the wall thickness of these portions of the inner and outer tubes 4 and 5 so that the diameter of the lumen 3 is substantially uniform or decreases at a smaller diminishing rate to the distal end of the catheter, the vascular catheter of the present invention has the following advantages: the rigidity of the catheter body 2 smoothly decreases to the distal end, and hence kink at the boundary between the tip portion 7 and the main portion 6 (boundary between the single-tube and double-tube structure portions) can be prevented with higher reliability; no step is formed in the outside surface at the boundary between the tip portion 7 and the main portion 6, and accordingly the catheter can be easily inserted into blood vessel without being caught by the entrance opening of a catheter guide or exerting excessive stimuli on the blood vessel or causing damage to the wall of the blood vessel; and the lumen 3 has a sufficiently large diameter up to the distal end with no narrowing nor step in the inside surface at the boundary between the single- and double-tube portions, and hence passing of a guide wire through the lumen 3 becomes easier and kink at the boundary is prevented.

The vascular catheter of the present invention is not limited to the structure of the catheter body 2 as described above, particularly as to the shapes of the inner and outer tubes which become smaller at different diminishing rates along the axis of the catheter toward the distal end. For example, the outer diameter of the catheter body 2 may be uniform or may become gradually smaller toward the distal end at a uniform diminishing rate, throughout the length of the catheter body 2.

When the taper 10 is formed at the distal end of the inner tube 4 as shown in FIG. 3, the tapered region is preferably within the range of about 0.5 to 2.0 mm and more preferably within the range of about 0.5 to 1.0 mm along the axis of the catheter body.

There is no particular limitation on the dimensions of the catheter body 2, and the dimensions of the catheter body 2 can be determined so as to be best suited for the purpose of the catheter.

For the vascular catheter used for cerebral blood vessel, example, the entire length of the catheter body 2 is preferably about 50 to 400 cm and more preferably about 70 to 150 cm. The length of the tip portion 7 is preferably about 5 to 30 cm and more preferably about 10 to 20 cm, The outer diameter of the catheter body 2 at the main portion 6 is preferably within the range of about 0.6 to 7.0 mm and more preferably within the range of about 0.7 to 6 mm. The outer diameter of the tip portion 7 is preferably within the range of about 0.3 to 1.0 mm and more preferably within the range of about 0.5 to 0.8 mm.

The wall thickness of the outer tube 5 at the main portion 6 is preferably within the range of about 5 to 300 μm and more preferably about 10 to 200 μm. The wall thickness of the tip portion 7 is preferably within the range of about 5 to 300 μm and more preferably abut 5 to 50 μm. The wall thickness of the inner tube 4 is preferably within the range of about 50 to 200 μm and more preferably abut 50 to 150 μm.

The inner tube 4 is formed of a metal or a alloy. Preferred examples of the metal include steel, tungsten, and copper. Preferred examples of the alloy include steel alloys such as austenitic stainless steel, for example SUS 304, SUS 316 and SUS 321, and marageing stainless steel, tungsten alloys, and copper alloys such as Cu-Zn alloys and Cu-Sn alloys. The austenitic stainless steel is more preferably.

Slits are formed in the metal or alloy tube by any of conventional techniques including laser machining (e.g., YAG laser), electric discharge machining, chemical etching, machining, and combinations thereof.

The outer tube 5 is preferably formed of a soft synthetic resin material The outer tube 5 is preferably more soft than the inner tube 4.

The resin material usable for the outer tube 5 includes thermoplastic resins such as polyolefins (e.g., polyethylene and polypropylene), polyolefin elastomers (e.g., ethylene elastomers, polypropylene elastomers, and ethylene-propylene copolymer elastomers), polyvinyl chloride, ethylene-vinyl acetate copolymers, polyamide elastomers, and polyurethane, and fluoro-resins, and silicone or latex rubber. Preferred are polyethylene, ethylene elastomers, polyamide elastomers, and polyurethane. Particularly when the catheter is applied to a catheter for administering an embolic substance (e.g., a dimethyl sulfoxide solution of cyanoacrylate or ethylene-vinyl alcohol copolymers) into a cerebral blood vessel, those synthetic materials which are insoluble in such solvents as dimethyl sulfoxide are preferred. Preferred synthetic resins for such catheters are solvent-resistant resins such as polyamide elastomers.

It is also preferred to incorporate into the synthetic resin of the outer tube 5 and tip member 5a to a radiopaque contrast substance in powder form, for example, elemental metals such as barium, tungsten and bismuth and compounds thereof. This facilitates the operator to locate the catheter over its entirety during insertion into a blood vessel.

The outside surface of the catheter may be coated with a biocompatible, especially anti-thrombotic, resin. Preferred anti-thrombotic resins are poly(hydroxyethyl methacrylate) and hydroxyethyl methacrylate-styrene copolymers (e.g., HEMA-St-HEMA block copolymers). Especially when a radiopaque contrast substance is mixed with a synthetic resin, such coating is preferred for eliminating the surface roughness associated with the radiopaque powder. While biocompatible resins are preferred, the same synthetic resin as used in forming the layer or tip member, but free of radiopaque powder may be thinly coated.

Also the catheter its outside surface is preferably treated so that the surface may exhibit lubricity when contacted with blood or body fluid. Such treatment include coating and fixation of hyclrophilic polymers such as poly(2-hydroxyethyl methacrylate), poly(hydroxyethyl acrylate), hydroxypropyl cellulose, methyl vinyl ether-maleic anhydride copolymers, polyethylene glycol, polyacrylamide, and polyvinyl pyrrolidone. Preferably the hydrophilic polymer layers have a thickness of 0.1 to 100 μm, more preferably 1 to 30 μm.

Further, the slit in the inner tube 4 may be filled with the resin material of the outer tube 5, though it is preferable that they are substantially left untilled, more preferable that they make spaces. The slit of the inner tube forms a space in the inner tube as shown in Figures. The outer tube 5 is normally formed of a uniform material for the whole, but may be formed of different materials for appropriately determined portions.

The rigidity (buckling strength) (ASTM D-790, at 23° C.) of the material for the outer tube 5 Is preferably within the range of 5 to 1,500 $kg/cm^2$ and more preferably 10 to 800 $kg/cm^2$. If the buckling strength of the material is less than 5 $kg/cm^2$, the catheter body 2 is too flexible to convey pushing force in the direction of the axis and turning force around the axis from the proximal portion to the distal end 13. Further, the difference between the rigidity of the single- and double-tube portions increases and the reluctance kinking at the boundary becomes too low. It is further preferred that a synthetic resin making the tip portion 5a of the outer tube 5 is softer than a synthetic resin making another portion of the outer tube.

Although the present invention is described above with reference to the embodiments shown in the drawings, the present invention is not limited to the structures of those embodiments and includes various modifications and variations. For example, the distal end portion of the inner tube 4 may be made of a material more elastic than that of the other portion of the inner tube 4. The inner surface of the inner tube may be covered by the above-mentioned synthetic resins.

Figure 4:
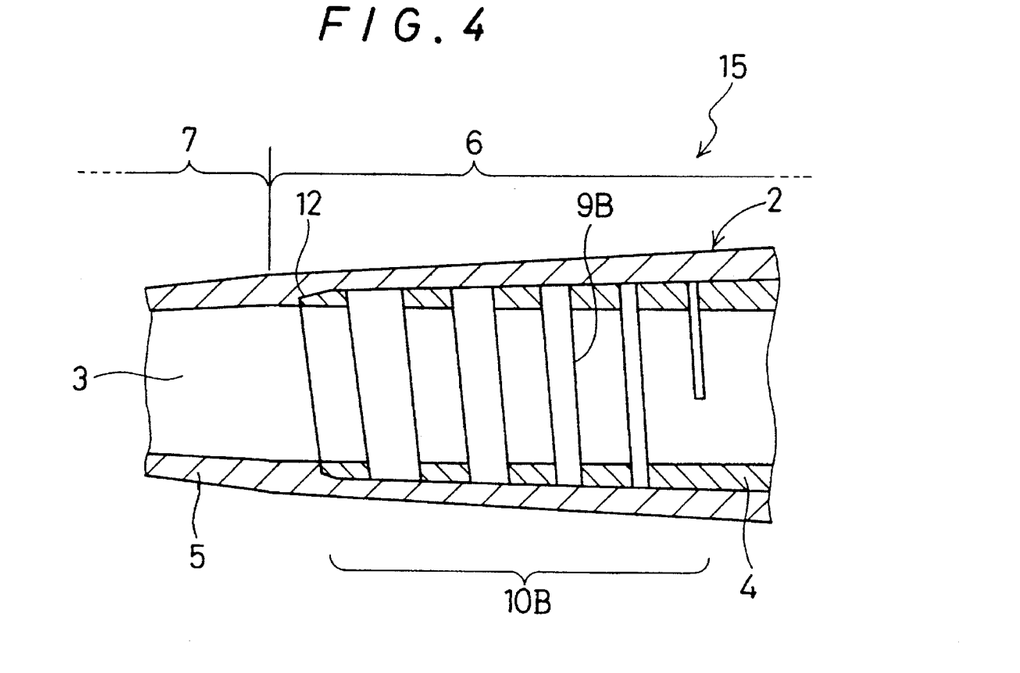
FIG. 4 is an enlarged longitudinal sectional view of the distal end portion of the vascular catheter of another embodiment of the present invention.

Next, the vascular catheter of the embodiment shown in FIG. 4 is described.

FIG. 4 is an enlarged cross-sectional view of the distal end portion of the vascular catheter of an embodiment of the present invention. The same parts as those of the catheter shown in FIG. 3 are designated by the same numerals and the description of them is omitted.

The vascular catheter 15 shown in FIG. 4 has another form of the slit in the inner tube. The slit 9B is a spiral slit whose width becomes gradually larger toward the distal end. By forming such a spiral slit, the flexibility of the portion around the distal end of the inner tube 4 increases more smoothly toward the distal end, which allows this portion of the catheter body 2 to bend in smooth curves and improves the manipulability of the catheter.

The width and the pitch of the spiral slit 9B of the catheter 15 of this embodiment is appropriately determined by taking into account the outer diameter of the inner or outer tube. The pitch of the slit 9B is preferably within the range of about 0.3 to 10 mm, and more preferably about 0.5 to 5 mm. The width of the slit 9B is preferably up to ⅔ times of the outer diameter of the inner tube 4. The width is preferably within the range of about 0.05 to 2.0 mm for the distal end portion of the slit portion 10B and about 0.01 to 0.5 mm for the proximal end portion. The width of the middle portion may be an intermediate value between the width of both end portions or may become gradually larger from the width of the proximal end portion to that of the distal end portion.

The catheters 1 and 15 have one slit 9A or 9B, but two or more slit may be formed the distal end portion of the inner tube. The proximal portion of the inner tube may, be made of a coil member without any spiral slit, and the distal portion of the inner tube may be made of the coil member having a spiral slit. The coil member may be made by a metal wire or a flat metal material.

Figure 5:
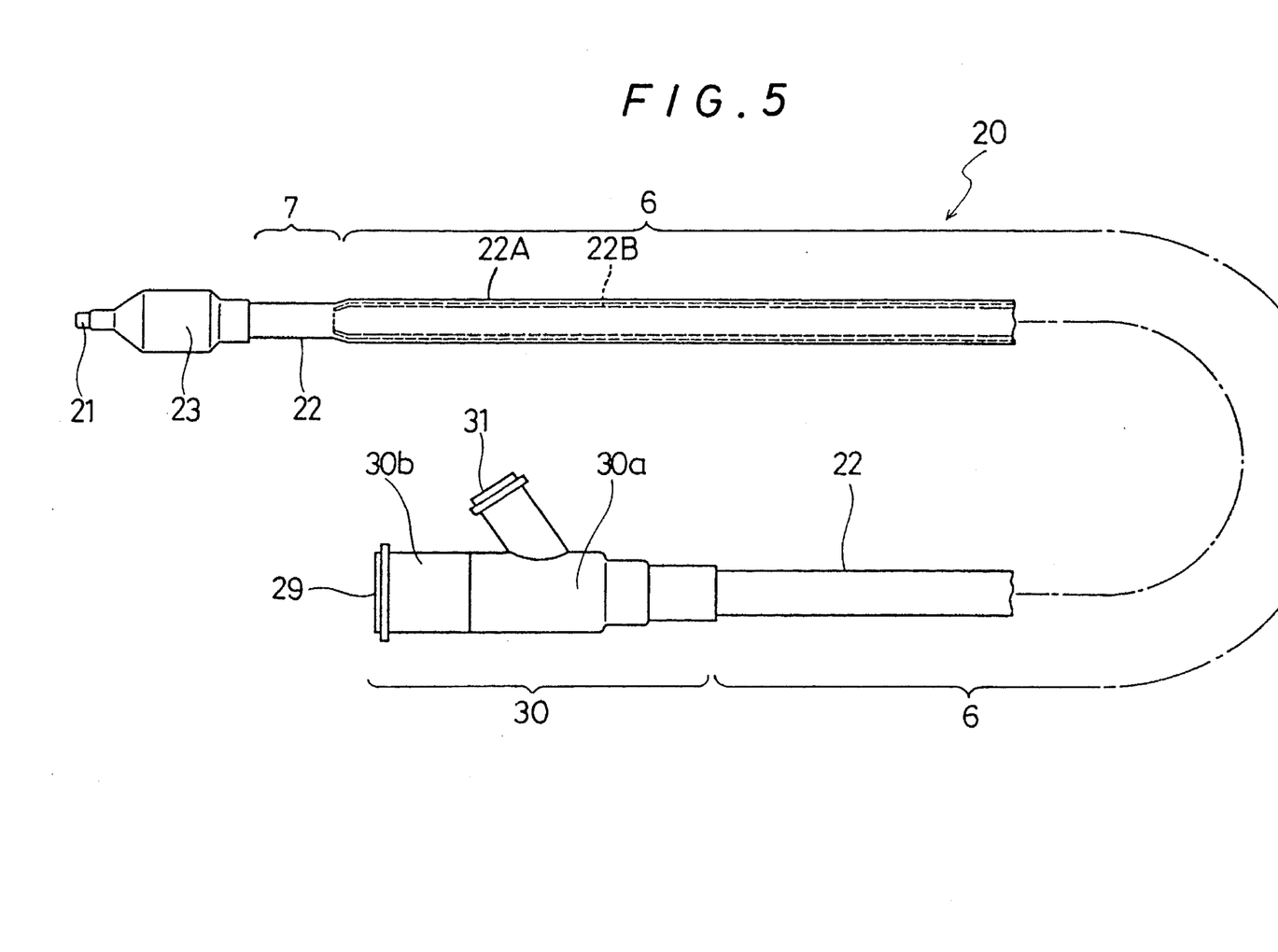
FIG. 5 is a plan view of an embodiment of the vascular dilatation instrument of an embodiment of the present invention.

Next, the vascular dilatation instrument of the embodiment shown in FIG. 5 is described.

Figure 6:
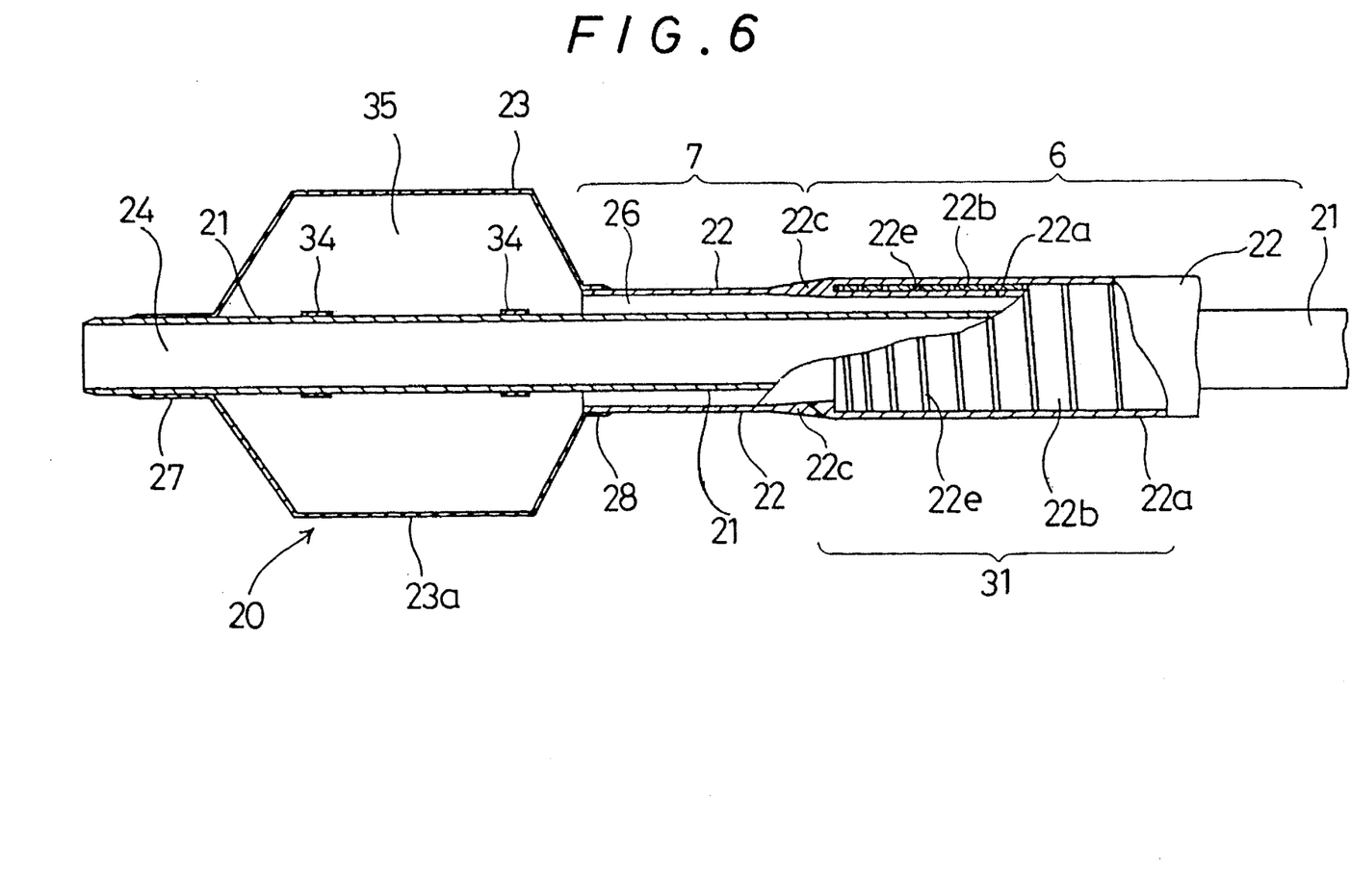
FIG. 6 is an enlarged longitudinal sectional view of the distal end portion of the vascular dilatation instrument shown in FIG. 5.

FIG. 5 is a plan view of an embodiment of the vascular dilatation instrument of an embodiment of the present invention. FIG. 6 is an enlarged longitudinal sectional view of the distal end portion of the vascular dilatation instrument shown in FIG. 5.

The vascular dilatation instrument 20 is defined as comprising an inner tube 21 defining a first lumen 24 extending between an open distal end and a proximal portion; an outer tube 22 disposed coaxially around the inner tube 21, having a distal end retracted a predetermined distance from the distal end of the inner tube and a proximal portion, and defining a second lumen 26 with the outside surface of the inner tube; an inflatable member or dilator 23 having one end attached to the inner tube 21 and another end attached to the outer tube 22 and defining an interior space in fluid communication with the second lumen 26 in the vicinity of the other end; a first opening 29 disposed in the proximal portion of the inner tube 21 in communication with the first lumen 24; and a second opening 31 disposed in the proximal portion of the outer tube 22 in fluid communication with the second lumen 26. At least one of the inner tube 21 and the outer tube 22 includes a main body section based on a tube made of metals or alloys and a distal section made of a synthetic resin. The metal or alloy tube 22b includes a spiral slit 22e.

The instrument 20 comprises a main body including an inner tube 21, an outer tube 22, and a dilator 23 and a branch hub or adapter 30.

The outer tube 22 of the vascular dilatation instrument 20 includes a main body portion 6 including a metal or alloy tube 22b and a distal portion 22c made of a synthetic resin. The metal or ahoy tube 22b includes a distal zone which forms a junction between the main body portion 6 and the distal portion 2c and is more flexible than the remainder of the metal tube.

More particularly, the outer tube 22 includes the metal or alloy tube 22b and a synthetic resin tube 22a enclosing and covering the outer and inner surfaces of the metal tube. The synthetic resin tube 22a protrudes beyond the distal end of the metal or ahoy tube 22b where it forms the distal portion 22c of the outer tube 22.

In the embodiment shown in FIG. 6, the pitch of the slit 22e becomes gradually smaller toward the distal end. By thus forming the slit 22e, the flexibility of the outer tube 22 increases gradually toward the distal end, and kink at the aforementioned boundary can be prevented with higher reliability. The pitch may be uniform throughout the length of the slit 22e.

The width and the pitch of the spiral slit 22e of the instrument 20 of this embodiment is appropriately determined by taking into account the outer diameter of the inner or outer tubes. The width is preferably within the range of about 1/1000 to 1/2 times of the outer diameter of the tube 22b. For a preferred embodiment, the width of the slit 22e is preferably within the range of about 0.01 to 0.5 mm and more preferably about 0.05 to 0.3 mm.

The pitch is preferably within the range of about 0.3 to 3 mm for the distal end portion of the slit portion 31 and about 5 to 10 mm for the proximal end portion. The pitch of the :middle portion may be an intermediate value between the pitches of both end portions or may become gradually smaller from the pitch of the proximal end portion to that of the distal end portion.

The length of the slit portion 31 ( the :length from the distal end of the metal or alloy tube to the proximal end of the silt) is preferably the range of about 100 to 1,000 mm and more preferably about 150 to 500 mm.

The slit 22e may be formed from the distal end of the metal or ahoy tube 22b or from a position at an appropriate distance from the distal end of the tube 22b as the slit 22e. The distance between the distal end of the tube 22b and that of the silt 22e is preferably up to 1.0 mm and more preferably up to 0.5 mm. The instrument of this embodiment has one slit 22e, but two or more slits may be formed the distal end portion of the inner tube.

The tip portion 22c is formed by the distal end portion of the outer tube 22 which extends beyond the distal end of the metal or alloy tube 22b.

The metal or ahoy tube 22b is formed of a metal or a ahoy. Preferred examples of the metal include steel, tungsten, and copper. Preferred examples of the alloy include steel alloys such as austenitic stainless steel, for example SUS 304, SUS 316 and SUS 321, and marageing stainless steel, tungsten alloys, and copper alloys such as Cu-Zn alloys and Cu-Sn alloys. The austenitic stainless steel is more preferably.

Slits are formed in the metal or ahoy tube by any of conventional techniques including laser machining (e.g., YAG laser), electric discharge machining, chemical etching, machining, and combinations thereof.

Typically the outer tube 22 has an outer diameter of 0.6 to 2.0 mm, preferably 0.8 to 1.6 mm. The difference between the outer diameter of the inner cube 21 and the inner diameter of the outer tube 22 is 0.05 to 2 mm, preferably 0.1 to 1.2 mm. The outer tube 22 has a wall thickness of 0.05 to 0.75 mm, preferably 0.07 to 0.3 mm.

For the synthetic resin tube 22a and the distal portion 22c of the outer tube 22, materials having a certain degree of flexibility are used, for example, thermoplastic resins such as polyolefins (e.g., polyethylene, polypropylene, and ethylene-propylene copolymers), polyvinyl chloride, ethylene-vinyl acetate copolymers, polyamide elastomers, and polyurethane, and silicone or latex rubber. Preferred are the thermoplastic resins, especially polyolefins and polyamide elastomers. That portion of the synthetic resin tube 22a surrounding and covering to the outer or inner surface of the metal or ahoy tube 22b preferably has a wall thickness of 5 to 300 μm, more preferably 10 to 200 mm. A synthetic resin making the distal portion (a tip member) 22c is softer than a synthetic resin making the synthetic resin tube 22a.

The outside surface of the outer tube 22 (more specifically, the outside surface of synthetic resin tube 22a) may be coated with a biocompatible, especially anti-thrombotic, resin. Preferred anti-thrombotic resins are poly(hydroxyethyl methacrylate) and hydroxyethyl methacrylate-styrene copolymers (e.g., HEMA-St-HEMA block copolymers).

Although part of the resin material of which the resin tube 22a is made may flow into the slits 22e in the metal or alloy tube 22b, it is preferred that the slits 22c be substantially free of the resin material and empty. In the absence of the resin material flowing into the slits, deformation of the metal or alloy tube 22b is never obstructed.

Alternatively, a heat-shrinkable tube may he used as the synthetic resin tube 22a of the outer tube 22. The heat-shrinkable tube used herein is a tube which has an inner diameter larger than the outer diameter of the metal or alloy tube 22b prior to heating and thus allows the metal or alloy tube to be inserted therethrough, but on heating, shrinks substantially uniformly over its entirety to come in close contact with the outside surface of the metal tube. Such a heat-shrinkable tube is preferably prepared by molding a resin into a tube having an inner diameter equal to or slightly smaller than the outer diameter of the metal or alloy tube, and expanding the tube over its entirety so as to increase its diameter so that upon heating, it may shrink to a diameter equal to or substantially equal to the diameter as molded. The heat-shrinkable tube is made of the material which can be expanded, but shrinks upon heating as mentioned above, for example, polyolefins (e.g., polyethylene, polypropylene, and ethylene-propylene copolymers), ethylene-vinyl acetate copolymers, and poyamide elastomers.

The inner tube 21 has an open distal end and defines the first lumen 24. The first lumen 24 longitudinally extends through the inner tube 21 for allowing a guide wire to be inserted into the tube and is in communication with the first opening 29 disposed in a branch hub 30 for defining a guide wire port. Typically the inner tube 21 has an outer diameter of 0.40 to 2.50 mm, preferably 0.55 to 2.40 mm and an inner diameter of 0.25 to 2.35 mm, preferably 0.30 to 1.80 mm.

Although the inner tube 21 has an identical diameter throughout its length in FIG. 6, the distal portion of the inner tube 21 may be tapered or reduced in diameter toward the distal end because tapering facilitates insertion of the vascular dilatation instrument into a vessel.

For the inner tube 21, materials having a certain degree of flexibility are used, for example, thermoplastic resins such as polyolefins (e.g., polyethylene, polypropylene, and ethylene-propylene copolymers), polyvinyl chloride, ethylene-vinyl acetate copolymers, polyamide elastomers, and polyurethane, and silicone rubber and latex rubber. Preferred are the thermoplastic resins, especially polyolefins.

The inner tube 21 is inserted through the outer tube 22 until the distal portion of the inner tube 21 protrudes beyond the outer tube 22 as shown in FIG. 6. As shown in FIG. 6, the outside surface of the inner tube 21 defines the second lumen 26 with the inside surface of the outer tube 22. The second lumen 26 then longitudinally extends from near the distal portion to the proximal end and has a sufficient volume. The second lumen 26 is in fluid communication on the distal side with the interior space of the inflatable member 23 and on the proximal side with the second opening 31 disposed in the branch hub 30 for defining an injection port for injecting a fluid (for example, vasographic contrast liquid) for inflating the dilator 23.

The inflatable member or dilator 23 is a contractible or foldable sleeve membrane so that it may be folded flat on the outside surface of the inner tube 21 in its deflated state. The inflatable member 23 includes a substantially cylindrical portion 23a having an approximately uniform diameter at least a part of which is substantially cylindrical, when inflated, for dilating the stricture in a blood vessel and is foldable in close contact with the inner tube 21 when deflated. The cylindrical portion 23a need not be completely cylindrical, but may be polygonal. The inflatable member 23 has one end 28 which is secured in a liquid tight manner to the distal end of the outer tube 22 by adhesion, fusion welding or the like and another end 27 which is similarly secured in a liquid tight manner to the distal portion of the inner tube 21. As shown in FIG. 6, the inflatable member 23 defines an interior space 35 between its inside surface and the outside surface of the inner tube 21 when inflated. The inflation interior space 35 is in fluid communication with the second lumen 26 at the one end 28 of the inflatable member 23 over its entire circumference. Since the inflatable member 23 at one end 28 is in communication with the second lumen 26 having a relative large volume, it is easy to inject a fluid into the inflatable member 23 interior space through the second lumen 26.

For the inflatable member 23, materials having flexibility and elasticity are used, for example, thermoplastic resins such as polyolefins (e.g., polyethylene, polypropylene, and ethylene-propylene copolymers), polyvinyl chloride, ethylene-vinyl acetate copolymers, crossinked ethylene-vinyl acetate copolymers, polyurethane, polyesters (e.g., polyethylene terephthalate), and polyamide elastomers, and silicone rubber and latex rubber. Preferred are the: thermoplastic resins.

The inflatable member 23 includes tapered transition portions between the cylindrical portion 23a and the opposed ends 27 and 28 attached to the inner and outer tubes 21 and 22, respectively. With respect to the dimensions of the inflatable member 23, the cylindrical portion 23a when inflated preferably has an outer diameter of 1.0 to 35.0 mm, more preferably 1.5 to 30.0 mm and a length of 10.0 to 80.0 mm, more preferably 15.0 to 75.0 mm. The inflatable member 23 preferably has an overall length of 15 to 120 mm, more preferably 20 to 100 mm.

Markers 34 are preferably provided on the outside surface of the inner tube 21. More particularly, as shown in FIG. 6, the markers 34 are disposed at a position rearward of and near the attachment between the dilator 23 and the inner tube 21 and a position forward of and near the attachment between the dilator 23 and the outer tube 22, that is, in alignment with the opposed ends of the cylindrical portion 23a. The markers 34 are made of a radiopaque material, for example, gold, platinum or alloys thereof. The provision of the markers 34 ensures easy location of the dilator 23 under radiological imaging. The markers 24 are preferably formed by fastening a ring of the above-mentioned metal around the inner tube 21 as by crimping whereby their clear radiographic images are always obtained.

In order to facilitate insertion of the vascular dilatation instrument 1 of the invention into a blood vessel or a guide: instrument, the outer tube 22 and dilator 23 on their outside surface are preferably treated so that the outside surface may exhibit lubricity when contacted with blood or body fluid. Such treatments include coating and fixation of hydrophilic polymers such as poly(2-hydroxyethyl methacrylate), poly-(hydroxyethyl acrylate), hydroxypropyl cellulose, methyl vinyl ether-maleic anhydride copolymers, polyethylene glycol, polyacrylamide, and polyvinyl pyrrolidone.

As shown in FIGS. 5 and 6, the branch hub or adapter 30 is attached to the proximal end of the instrument. The branch hub 30 includes fixedly mated inner and outer hub segments 30a and 30b. The inner hub segment 30b is fixedly connected to proximal end of the inner tube 21 and has the first opening 29 in communication with the first lumen 24 and forming a guide wire port. The outer hub segment 30a is fixedly connected to proximal end of the outer tube 22 (which is a composite body of synthetic resin tube 22a and metal or ahoy tube 22b) and has the second opening 31 in communication with the second lumen 26 and forming an injection port. The branch hub 30 is made of thermoplastic resins such as polycarbonates, polyamides, polysuffones, polyarylates, and methacrylate-butylene-styrene copolymers. Instead of the branch hub 30, tubing sections each having a port member defining an opening at a proximal end may be liquid-tightly attached to the first and second lumens, respectively. The structure of the vascular dilatation instrument is not limited to that shown in FIGS. 5 and 6.

Figure 7:
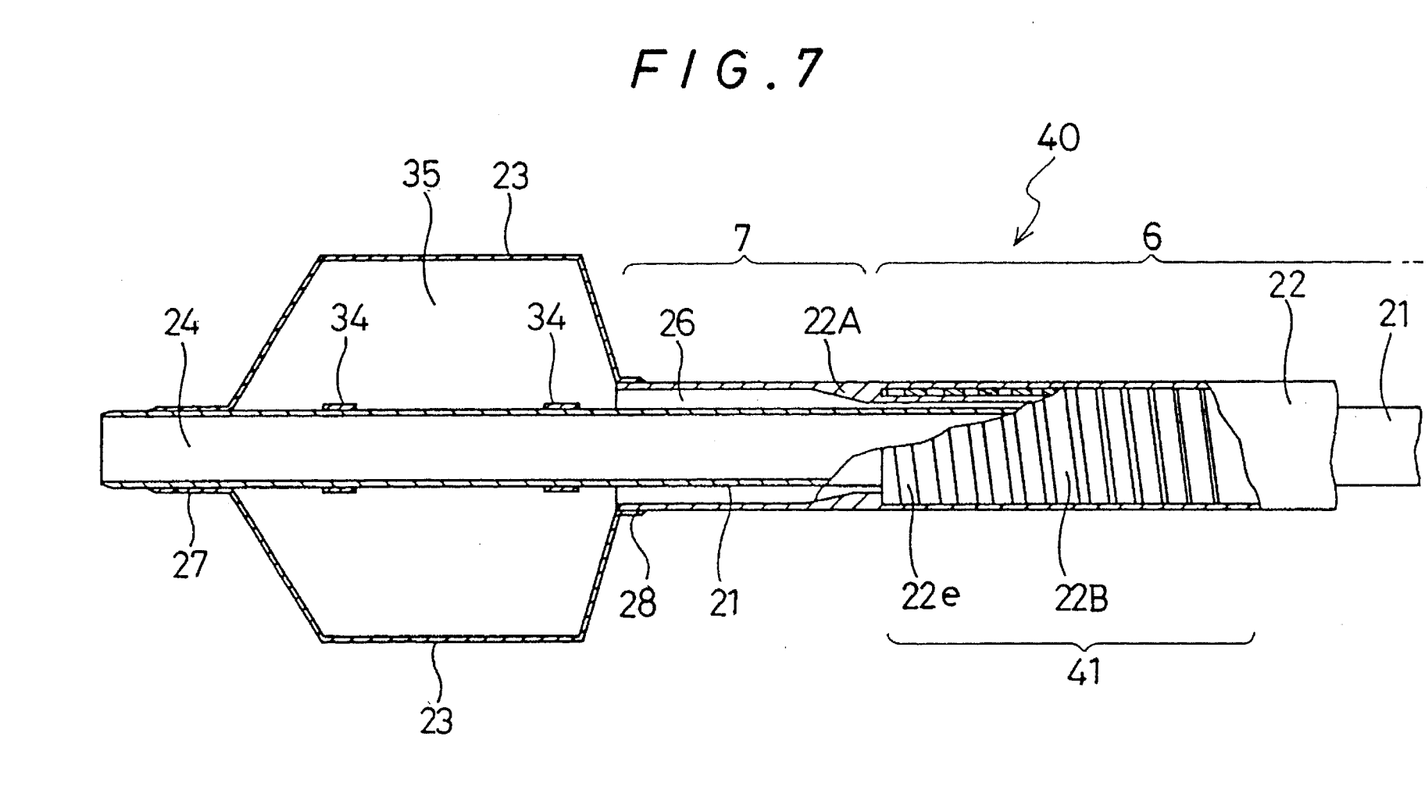
FIG. 7 is an enlarged longitudinal sectional view of the distal end portion of the vascular dilatation instrument of another embodiment of the present invention.

Next, the vascular dilatation instrument of the embodiment shown in FIG. 7 is described.

FIG. 7 is an enlarged cross-sectional view of the distal end portion of the vascular catheter of an embodiment of the present invention. The same parts as those of the catheter shown in FIG. 6 are designated by the same numerals and the description of them is omitted.

In the vascular dilatation instrument 40, the metal or alloy tube 22b is provided with a spiral slit 22e having a width which is greater at the distal end and smaller at the proximal end of the distal zone( the slit portion). The slit width is preferably gradually reduced from the distal end toward the proximal end. The width of the spiral slit 22e becomes gradually larger toward the distal end. By forming such a spiral slit, the flexibility of the portion around the distal end of the tube 22b increases more smoothly toward the distal end, which allows this portion of the catheter body 6 to bend in smooth curves and improves the manipulability of the catheter.

The width and the pitch of the spiral slit 22e of the instrument 40 of this embodiment is appropriately determined by taking into account the outer diameter of the outer tube 22. The pitch of the slit 22e is preferably within the range of about 0.3 to 10 mm, and more preferably about 0.5 to 5 mm. The width of the slit 22e is preferably up to 2/3 times of the outer diameter of the metal or alloy tube 22b. The width is preferably within the range of about 0.05 to 2.0 mm for the distal end portion of the slit portion 41 and about 0.01 to 0.5 mm for the proximal end portion. The width of the middle portion may be an intermediate value between the width of both end portions or may become gradually larger from the width of the proximal end portion to that of the distal end portion. The length of the slit portion 41 ( the length from the distal end of the metal or alloy tube to the proximal end of the slit) is preferably the range of about 100 to 1,000 mm and more preferably about 150 to 500 mm.

The instruments 20 and 40 have one slit 22e, but two or more slit may be formed the distal end portion of the metal or alloy tube. The proximal portion of the metal or alloy tube may be made of a coil member without any spiral slit, and the distal portion of the inner tube may be made of the coil member having a spiral slit. The coil member may be made by a metal or ahoy wire or a flat metal or ahoy material.

EXAMPLE

Examples of the instrument according to the invention are given below by way of illustration and not by way of limitation.

Example 1

A catheter as shown in FIGS. 1 to 3 was fabricated. A pipe of stainless steel (SUS 304) was worked into an ahoy tube having an outer diameter of 1.0 mm, an inner diameter of 0.85 mm, and a length of 100 cm. A spiral slit was cut in a distal zone of the alloy tube which extended 20 cm from the distal end, using a YAG laser machine model ML-4140A (Miyachi Technos K., laser irradiation at a power of 4 W and an irradiation rate of 10 mm/min.). The spiral slit had a constant width of 0.5 mm and a pitch which gradually increased from 1 mm at the distal end to 10 mm at the terminus. The ahoy tube including the slit portion was covered on both the inside and outside surfaces with polyethylene( Mitsubishi Yuka K.K. EY40H). The polyethylene coating did not substantially flow into the slit and the slit remained empty. The resin coated ahoy tube constituted a instrument main body section. The resin layer covering the metal tube was 0.04 mm thick on the out side and 0.03 mm on the inside. The instrument main body section was 1.08 mm in outer diameter and 0.79 mm in inner diameter.

A tip member constituting a catheter distal section was molded from polyethylene which is more flexible than polyethylene (EY40H) to a length of 20 cm, an outer diameter of 0.9 mm and an inner diameter of 0.8 mm. The tip member was connected to the distal end of the resin-coated ahoy tube by fusion welding.

A hub as shown in FIG. 2 was molded from polycarbonate and adhesively joined to the proximal end of the resin-coated alloy tube, completing the catheter.

The catheter was measured for modulus of elasticity at different positions. For measurement, Autograph AGS-100D manufactured by Shimazu Mfg. K.K. was used. Measurement was done by setting a pair of rods having a diameter of 5 mm at a center-to-center distance of 25 mm, resting a selected area of the instrument on the rods, and loading the span portion by means of a pusher having a semi-spherical lower end.

Test conditions are shown below.

Test mode: cycle (down start)

Load cell: 5000 gf

F.S. lead: 2500 gf (×2)

Test speed: 5 mm/min.

Minimum stroke: 0.00 mm stop

Maximum stroke: 2.00 mm return

Chart control: X-P C (×50)

The results of measurements are shown in Table 1.

TABLE 1

| Catheter | Load |
| --- | --- |
| Main body section, no slit area | 780 g |
| Main body section, slit, 10 mm pitch area | 532 g |
| Main body section, slit, 5 mm pitch area | 230 g |
| Main body section, slit, 2 mm pitch area | 36 g |
| Distal section (solely polyethylene) | 11 g |

Example 2

A vascular dilatation instrument as shown in FIGS. 5 and 6 was fabricated. An outer tube was made as follows. A pipe of stainless steel (SUS304) was worked into an alloy tube having an outer diameter of 1.0 mm, an tuner diameter of 0.9 mm, and a length of 100 cm. A spiral slit was cut in a distal zone of the alloy tube which extended 70 cm from the distal end, using a YAG laser machine model ML-4140A (Miyachi Technos K.K., laser irradiation at a power of 4 W and an irradiation rate of 10 mm/min.). The spiral slit had a constant width of 0.5 mm and a pitch which gradually increased from 1 mm at the distal end to 10 mm at the terminus. The ahoy tube including the slit portion was covered on both the inside and outside surfaces with polyethylene( Mitsui Sckiyu Kagaku K.K. HYZEX3000B). The polyethylene coating did not substantially flow into the slit and the slit remained empty. The resin coated ahoy tube constituted an outer tube. The resin layer covering the alloy tube was 0.1 mm thick on the outside and 0.05 mm on the inside. A main body section of the outer tube was 1.2 mm in outer diameter and 0.8 mm in inner diameter. A tip member constituting the outer tube distal section was molded from polyethylene which is more-flexible than polyethylene (HYZEX3000B) to a length of 30 cm, an outer diameter of 1 mm and an inner diameter of 0.8 mm. The tip member was connected to the distal end of the resin-coated alloy tube by fusion welding.

An inner tube was molded from polyethylene to a length of 135 cm, an outer diameter of 0.6 mm and an inner diameter of 0.5 mm.

An inflatable member was made from polyethylene terephthalate by blow molding. An inner tube hub and an outer tube hub were molded from polycarbonate and adhesively joined to the proximal end of the tubes. The inner tube was inserted into the outer tube. A tip portion of the inflatable member was fitted to a tip portion of the inner tube. An end portion of the inflatable member was fitted to a tip portion of the outer tube. The inner tube hub was fitted to the outer tube hub, completing the instrument.

The instrument was measured for modulus of elasticity at different positions. For measurement. Autograph AGS-100D manufactured by Shimazu Mfg. K.K. was used. Measurement was done by setting a pair of rods having a diameter of 5 mm at a center-to-center distance of 25 mm, resting a selected area of the instrument on the rods, and loading the span portion by means of a pusher having a semi-spherical lower end. Test conditions are shown below.

Test mode: cycle (down start)
Load cell: 5000 gf
F.S. load: 2500 gf (×2)
Test speed: 5 mm/min.
Minimum stroke: 0.00 mm stop
Maximum stroke: 2.00 mm return
Chart control: X-P C (×50)

The results of measurements are shown in Table 2.

TABLE 2

| Instrument | Load |
| --- | --- |
| Main body section, no slit area | 780 g |
| Main body section, slit, 10 mm pitch area | 532 g |
| Main body section, slit, 5 mm pitch area | 230 g |
| Main body section, slit, 2 mm pitch area | 36 g |
| Distal section of the outer tube (solely polyethylene) | 11 g |

As is evident from Tables 1 and 2, the catheter and instrument of the invention have a gradual change in physical property from the main body portion of the alloy tube to the most distal end of the catheter or the outer tube of the instrument through the alloy tube distal zone.

As described above the vascular catheter of this invention can bend more easily along a guide wire and blood vessels than conventional catheters because of the structure of the catheter body having the proximal main portion made up of double tubes and the distal tip made up of a single tube and the higher flexibility of the distal end portion of the inner tube increased by a spiral slit. The vascular catheter of this invention hence has a higher reluctance to kicking, exerts smaller stimuli on blood vessels, causes less damage to the wall of blood vessels, improved manipulability, and higher safety than conventional catheters.

There has been described a vascular dilatation instrument having a fully flexible distal zone and capable of transmitting translational and torsional forces from the proximal end to thee distal end of it (improved in pushability and torque transmission). The distal zone of the metal or alloy tube is more flexible and deformable than the main body portion. The flexible distal zone of the metal tube provides a smooth transition from the main body portion to the leading resinous portion. When a load is applied to the transition between the relatively stiff main body portion and the relatively flexible distal portion, the distal portion follows the load and deforms in the loading direction. This prevents angular folding at the transition which would otherwise occur due to the difference in physical properties between the metal tube and the synthetic resin. The spiral slit is formed in the distal zone of the metal tube, the distal zone becomes more flexible and bendable. This minimizes the difference in physical properties between the metal tube and the synthetic resin layer, eliminating separation and differential motion therebetween. The catheter instrument is thus more smooth and effective to manipulate.

Although some preferred embodiments have been described, many modifications and variations may be made thereto in the light of the above teachings. It is therefore to be understood that within the scope of the appended claims, the invention may be practiced otherwise than as specifically described.

We claim:

1. A vascular dilatation instrument comprising
    an inner tube defining a first lumen extending between an open distal end and a proximal portion,
    an outer tube disposed coaxially around said inner tube, having a distal end retracted a predetermined distance from the distal end of said inner tube and a proximal portion, and defining a second lumen with the outside surface of said inner tube,
    an inflatable member having one end attached to said inner tube and another end attached to said outer tube, and defining an interior space in fluid communication with said second lumen in the vicinity of the other end,
    a first opening disposed in the proximal portion of said inner tube in communication with said first lumen, and
    a second opening disposed in the proximal portion of said outer tube in fluid communication with said second lumen,
    wherein at least one of said inner tube and said outer tube includes a main body section based on a tube formed of a metal selected from the grope consisting of steel, tungsten and copper or a alloy selected from the grope of steel alloy, tungsten alloy and copper ahoy and a distal section made of a synthetic resin, the tube made of said metal or said alloy has one or more spiral slits in the distal end portion.

2. A vascular dilatation instrument according to claim 1 wherein said outer tube includes said metal or alloy tube and a synthetic resin tube covering the surface of said metal or alloy tube, said synthetic resin tube protruding beyond the distal end of said rectal or alloy tube to form the distal section of said outer tube.

3. A vascular dilatation instrument according to claim 1 wherein said spiral slit is gradually reduced in pitch toward the distal end of said metal or alloy tube.

4. A vascular dilatation instrument according to claim 1 wherein said spiral slit is gradually increased in width toward the distal end of said metal or alloy tube.

5. A vascular dilatation instrument according to claim 1 wherein an distal section is formed of a synthetic resin, and the synthetic resin of said distal section is softer than the synthetic resin of said covering the surface of said metal or ahoy tube.

6. A vascular dilatation instrument according to claim 1 wherein said slit forms a space in said outer tube.

\* \* \* \* \*

UNITED STATES PATENT AND TRADEMARK OFFICE
CERTIFICATE OF CORRECTION

PATENT NO. : 5,569,200
DATED : October 29, 1996
INVENTOR(S) : Akihiko UMENO, et al.

It is certified that error appears in the above-indentified patent and that said Letters Patent is hereby corrected as shown below:

In Column 1, line 62, delete "ahoy" and insert --alloy--

In Column 2, line 21, delete "ahoy" and insert --alloy--

In Column 3, line 44, delete "1.00" and insert --1.00 mm.--

In Column 6, line 1, delete "treatment" and insert --treatments--

In Column 6, line 2, delete "hyclrophilic" and insert --hydrophilic--

In Column 6, line 11, delete "untilled" and insert --unfilled--

In Column 6, line 25, delete "reluctance kinking" and insert --reluctance to kinking--

In Column 7, line 7, delete "fiat" and insert --flat--

In Column 7, line 40, delete "ahoy" and insert --alloy--

In Column 7, line 48, delete "ahoy" and insert --alloy--

In Column 8, line 11, delete "ahoy" and insert --alloy--

In Column 8, line 21, delete "ahoy" (both occurrences) and insert --alloy--

In Column 8, line 29, delete "ahoy" and insert --alloy--

In Column 8, line 35, delete "cube" and insert --tube--

In Column 8, line 49, delete "ahoy" and insert --alloy--

In Column 8, line 51, delete "10 to 200 mm" and insert --10 to 200 $\mu$m--

In Column 8, line 62, delete "22c" and insert --22e--

In Column 9, line 17, delete "poyamide" and insert --polyamide--

In Column 9, line 53, delete "fiat" and insert --flat--

UNITED STATES PATENT AND TRADEMARK OFFICE
CERTIFICATE OF CORRECTION

PATENT NO. : 5,569,200
DATED : October 29, 1996
INVENTOR(S) : Akihiko UMENO, et al.

It is certified that error appears in the above-indentified patent and that said Letters Patent is hereby corrected as shown below:

In Column 10, line 12, delete "copelymers" and insert --copolymers--
In Column 10, line 62, delete "ahoy" and insert --alloy--
In Column 11, line 46, (twice) delete "ahoy" and insert --alloy--
In Column 11, line 57, delete "ahoy" and insert --alloy--
In Column 11, line 61, delete "Technos K.," and insert --Technos K.K.,--
In Column 11, line 65, delete "ahoy" and insert --alloy--
In Column 12, line 2, delete "ahoy" and insert --alloy--
In Column 12, line 12, delete "ahoy" and insert --alloy--
In Column 12, line 27, delete "lead" and insert --load--
In Column 12, line 49, delete "tuner" and insert --inner--
In Column 12, line 56, delete "ahoy" and insert --alloy--
In Column 12, line 58, delete "Sckiyu" and insert --Sekiyu--
In Column 12, line 61, delete "ahoy" and insert --alloy--
In Column 14, line 42, delete "ahoy" and insert --alloy--
In Column 14, line 49, delete "rectal" and insert --metal--

UNITED STATES PATENT AND TRADEMARK OFFICE
CERTIFICATE OF CORRECTION

PATENT NO. : 5,569,200

DATED : October 29, 1996

INVENTOR(S) : Akihiko UMENO, et al.

It is certified that error appears in the above-indentified patent and that said Letters Patent is hereby corrected as shown below:

In Column 14, line 61, delete "ahoy" and insert --alloy--

Signed and Sealed this

Twenty-first Day of January, 1997

Attest:

BRUCE LEHMAN

*Attesting Officer*  *Commissioner of Patents and Trademarks*